(12) United States Patent
Okumura et al.

(10) Patent No.: US 6,426,091 B1
(45) Date of Patent: Jul. 30, 2002

(54) SUSTAINED-RELEASE THEOPHYLLINE TABLET

(75) Inventors: Mutsuo Okumura; Minoru Kamakura; Masaaki Sunohara, all of Omiya (JP)

(73) Assignee: Nikken Chemicals Co., Ltd., Tokyo (JP)

( * ) Notice: Subject to any disclaimer, the term of this patent is extended or adjusted under 35 U.S.C. 154(b) by 0 days.

(21) Appl. No.: 09/509,322

(22) PCT Filed: Sep. 21, 1998

(86) PCT No.: PCT/JP98/04247

§ 371 (c)(1),
(2), (4) Date: Mar. 21, 2000

(87) PCT Pub. No.: WO99/16448

PCT Pub. Date: Apr. 8, 1999

(30) Foreign Application Priority Data

Sep. 30, 1997 (JP) .............................................. 9-281172
Aug. 21, 1998 (JP) ........................................... 10-235406

(51) Int. Cl.⁷ ............................ A61K 9/22; A61K 9/28; A61K 9/32; A61K 9/30
(52) U.S. Cl. ....................... 424/468; 424/464; 424/465; 424/490; 424/495; 424/497; 424/474; 424/482
(58) Field of Search ................................ 424/464, 465, 424/490, 494, 495, 497, 486, 487

(56) References Cited

U.S. PATENT DOCUMENTS

| 3,860,733 | A | 1/1975 | Morse et al. | 426/302 |
| 4,590,062 | A | 5/1986 | Jang | 424/19 |
| 4,692,337 | A | 9/1987 | Ukigaya et al. | |
| 5,169,642 | A | 12/1992 | Brinker et al. | 424/488 |
| 5,268,182 | A | 12/1993 | Brinker et al. | 424/488 |
| 5,593,690 | A * | 1/1997 | Akiyama et al. | 424/457 |

FOREIGN PATENT DOCUMENTS

| JP | 56-122311 | 9/1981 |
| JP | 57-53325 | 11/1982 |
| JP | 2 138210 | 5/1990 |
| JP | 3 190817 | 8/1991 |
| JP | 3 193733 | 8/1991 |
| JP | 3 193734 | 8/1991 |
| JP | 6 293635 | 10/1994 |
| JP | 07 29927 | 4/1995 |

* cited by examiner

Primary Examiner—Thurman K. Page
Assistant Examiner—Rachel M. Bennett
(74) Attorney, Agent, or Firm—Christie, Parker & Hale, LLP

(57) ABSTRACT

A theophylline sustained release tablet obtained by coating core granules composed mainly of theophylline with a layer of a coating film composed of a hydrophobic material and a plastic excipient and optionally containing an enteric polymer material to form coated granules and then by compressing the coated granules together with a disintegrating excipient.

13 Claims, 3 Drawing Sheets

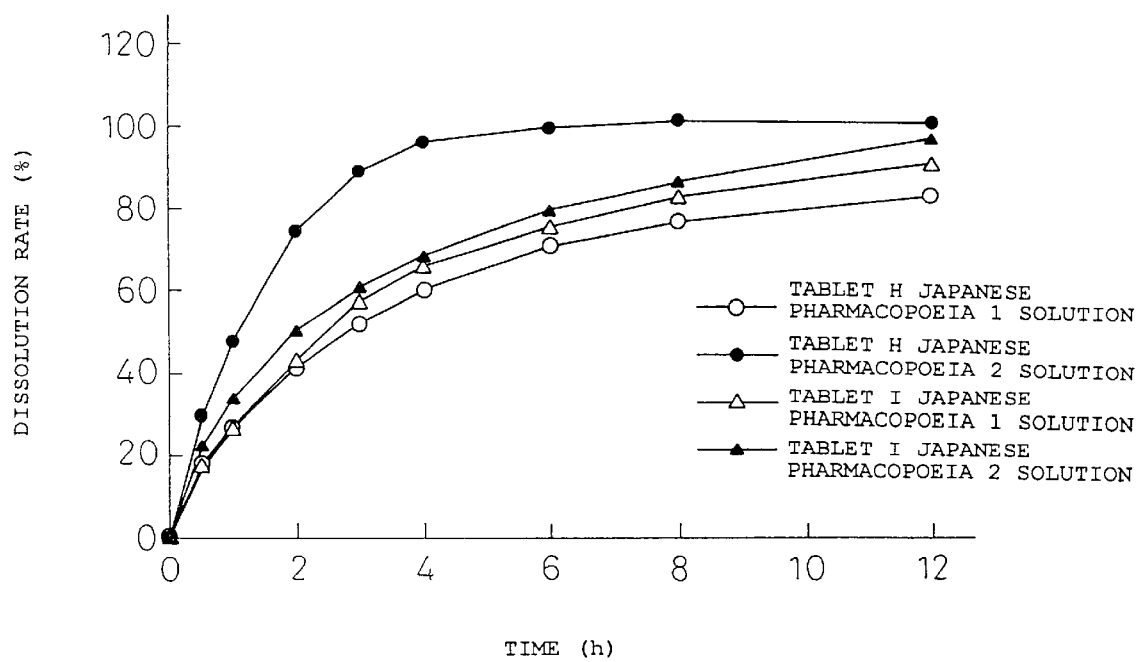

SUSTAINED-RELEASE THEOPHYLLINE TABLET

This application is a 371 of PCT/JP98/04247 filed Sep. 21, 1998.

TECHNICAL FIELD

The present invention relates to a theophylline sustained release tablet and, more specifically it relates to a multi unit type sustained release tablet.

BACKGROUND ART

Theophylline is a useful medicine frequently used as an agent for treating symptoms of bronchial asthma. It is known in the art that its range of effective blood level is about 10 to 20 μg/ml. However, if the concentration of theophylline in the blood exceeds 20 μg/ml, it is pointed out that serious side effects sometimes appear with regard to the cardiovascular system and the central nervous system. Further, there is a large difference in blood levels among individuals. Various conditions (e.g., cardiac insufficiency, liver and kidney disease, etc.), age differences, smoking, etc. also have large effects. Further, theophylline has a short biological half-life of about 6 hours for adults. In order to maintain the effective blood level, four times doses per day have been considered necessary. However, such frequent dosage is troublesome to patients, reduces patient compliance, and causes the state of the disease to become worse. In particular, attacks of bronchial asthma often occur at daybreak. It is not possible to sufficiently prevent such attacks with just ingestion before going to bed, and therefore, repeat ingestion close to daybreak is necessary. Thus, in the past, continuous effort has been made to develop a sustained release type theophylline formulation. Several formulations are already available on the market.

Among the theophylline sustained release formulations known up to now, there have been those of the type dispersing the medicament in a matrix composed of an insoluble synthetic resin or lipid (for example, Japanese Unexamined Patent Publication (Kokai) No., 56-122311, U.S. Pat. No. 4,590,062, etc.), those having a structure where beads having various types of different release rates are contained in capsules or tablets and these beads are formed with alternative layers of active ingredients and layers of insoluble lipid around a core (for example, U.S. Pat. No. 3,860,733), etc. Among these theophylline sustained release formulations, there are those which are already marketed, but each has defects which cannot be ignored in actual use. None of these types can be said to be perfected yet as sustained release formulations.

That is, the former types of formulations had the defect that, since the ratio of the vehicle and excipient for the dispersion of the medicament reached as high as 50% or more, a reduction in the content of the medicament and an increase in the size of the tablet could not be avoided and, further, the medicament was not released perfectly. Further, the latter types of formulations had the defect that they required a high degree of skill, since the complicated operations are necessary for the formulation thereof, and therefore, the manufacturing costs also became high.

The present inventors previously proposed sustained release formulations for theophylline in Japanese Examined Patent Publication (Kokoku) No. 57-53325, Japanese Unexamined Patent Publication (Kokai) No. 3-193733, and Japanese Examined Patent Publication (Kokoku) No. 07-29927.

SUMMARY OF THE INVENTION

Accordingly, the present invention is to provide a formulation of a multi unit type for which those dose a day is sufficient and for which formulation is easy.

The present inventors engaged in intensive study to achieve the above-mentioned object of the present invention and, as a result, found that it is possible to make the size of the tablet smaller than the conventional theophylline formulations and further to obtain a tablet having a superior sustained release effect whereby the present invention is completed.

Thus, in accordance with the present invention, there is provided a theophylline sustained release tablet characterized in the core granules composed mainly of theophylline are made into coated granules coated with at least one coating film layer composed of a hydrophobic material and a plastic excipient and, optionally, containing an enteric polymer material and the coated granules are then compressed together with a disintegrating excipient.

BRIEF DESCRIPTION OF THE DRAWINGS

The present invention will now be described in further detail with reference to the attached drawings.

FIG. 5 is a graph showing the results of dissolution test of a tablet H and a tablet I obtained in Example 8 (i.e., second method, 50 revolutions, Japan Pharmacopoeia 1 solution and Japanese Pharmacopoeia No. 2 solution).

BEST MODE FOR CARRYING OUT THE INVENTION

Figure 1:
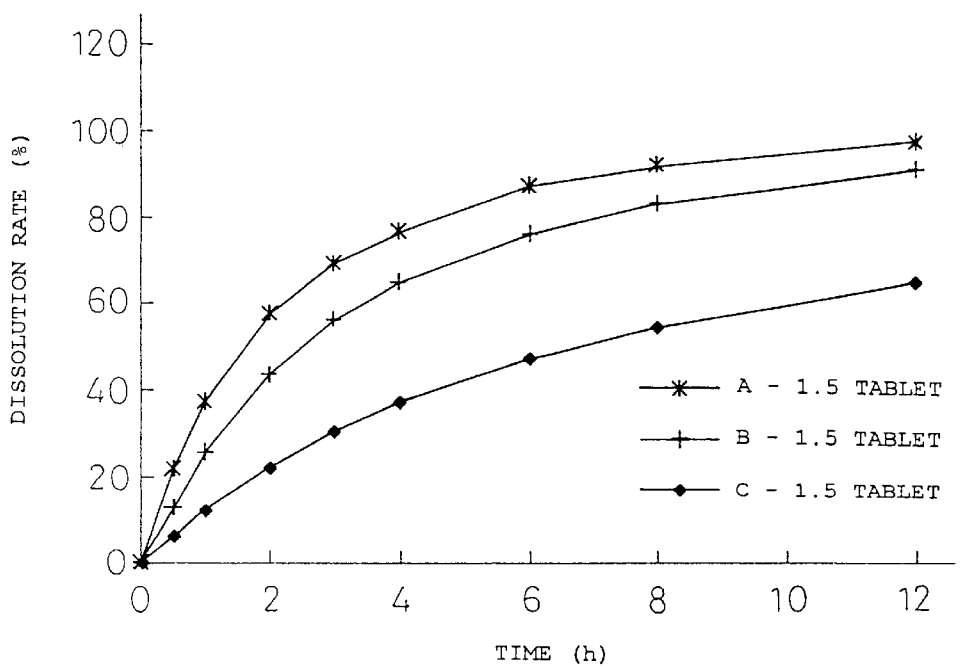
FIG. 1 is a graph showing the results of dissolution test of a tablet A-1.5 to a tablet C-1.5 obtained in Example 1 (second method, 50 revolutions, Japanese Pharmacopoeia 2 solution).
Figure 2:
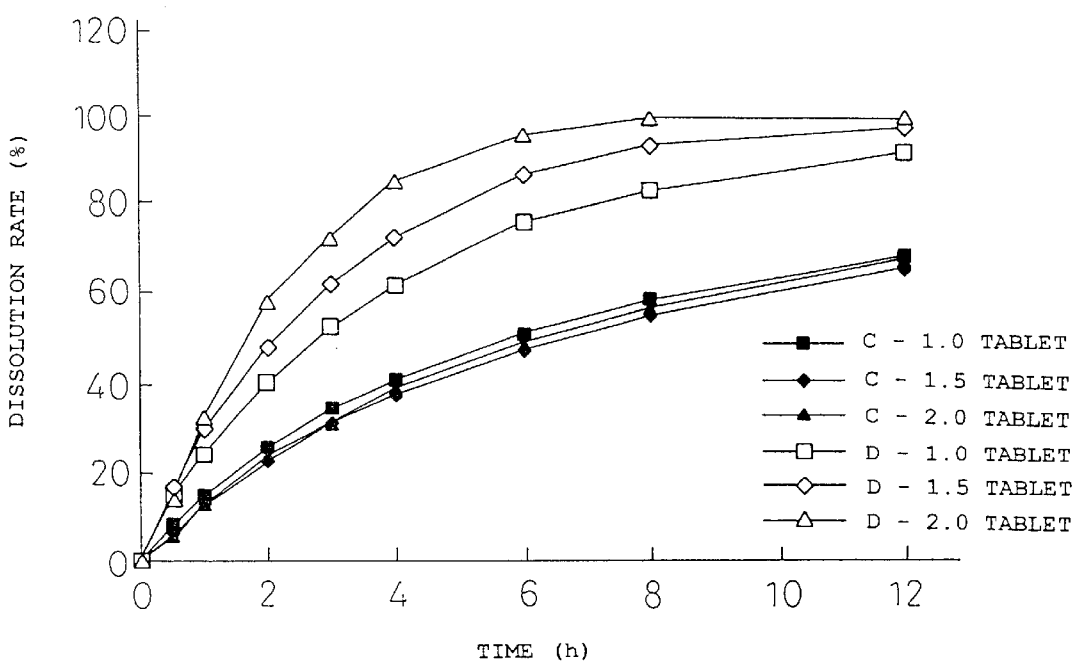
FIG. 2 is a graph showing the results of dissolution test of tablets obtained in Example 2 and Example 4 (i.e., the second method, 50 revolutions, Japanese Pharmacopoeia 2 solution).
Figure 3:
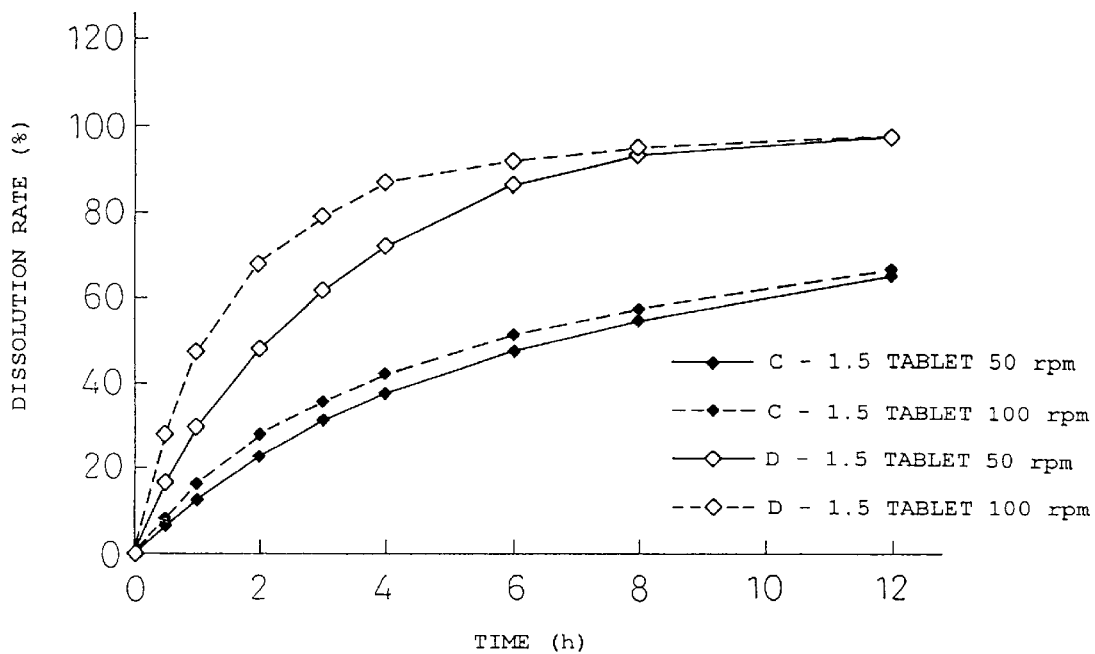
FIG. 3 is a graph showing the results of dissolution testing of a tablet C-1.5 and a tablet D-1.5 obtained in Example 1 and Example 3 (i.e., the second method, 50 and 100 revolutions, Japanese Pharmacopoeia 2 solution).

The core granules composed mainly of theophylline used in the present invention are those where the major part of the core granules is composed of theophylline and the relative hardness is high, preferably those having a particle size of 50 to 1700 μm, more preferably 355 to 1400 μm, more preferably 425 to 1000 μm. The core granules are specifically composed of theophylline, a lubricant such as magnesium stearate, calcium stearate, light anhydrous silicic acid, and hydrous silicon dioxide, and a dissolution aid such as sodium laurosulfate, a sucrose fatty acid ester, and glyceryl monostearate and have ratios of the lubricant and dissolution aid based upon 100 parts by weight of theophylline of respectively less than about 1 part by weight. The core granules composed mainly of theophylline may be prepared by homogeneously mixing these powders and then applying a general dry granulation method, etc.

In accordance with the present invention, the coating agent for forming the coating film or the coating layer coating the core granules composed mainly of theophylline may be prepared by mixing and dispersing into 100 parts by weight of a solvent such as a lower alcohol (e.g., ethanol) a hydrophobic material in an amount of preferably 3 to 10 parts by weight, more preferably 3 to 8 parts by weight, and a plastic excipient in an amount, based upon 100 parts by weight of the hydrophobic material, of preferably 10 to 50 parts by weight, more preferably 10 to 30 parts by weight or may be prepared by mixing and dispersing into 100 parts by weight of a solvent such as a lower alcohol, a hydrophobic material in an amount of preferably 3 to 10 parts by weight, more preferably 3 to 8 parts by weight, an enteric polymer material in an amount, based upon 100 parts by weight of the hydrophobic material, of preferably 5 to 150 parts by weight, more preferably 10 to 100 parts by weight, and a plastic excipient in an amount, based upon 100 parts by weight of the hydrophobic material, of preferably 10 to 50 parts by weight, more preferably 10 to 30 parts by weight. Alternatively, commercially available aqueous ethylcellulose (Aquacoat®, Asahi Kasei or Surelease®, Colorcon), ethyl acrylate-methyl methacrylate copolymer (Eudragit NE®, Rohm), a methacrylate copolymer (Eudragit L30D®, Rohm), and hydroxypropylmethylcellulose phthalate (HP-50, 55, Shinetsu Chemical), and other coating solutions may be used.

As the hydrophobic material used in the coating solution, for example, ethylcellulose, an ethyl acrylate-methyl methacrylate copolymer, aminoalkyl-methacrylate copolymer, etc. may be mentioned, preferably ethylcellulose or an ethyl acrylate-methyl methacrylate copolymer may be mentioned.

As the plastic excipient, for example, triethyl citrate, a glyceryl fatty acid ester, cetanol, hardened castor oil, hardened rapeseed oil, carnauba wax, etc. may be used, preferably triethyl citrate or cetanol may be used.

As the enteric polymer material, for example, a methacrylate copolymer, hydroxypropylmethylcellulose phthalate, hydroxypropylmethylcellulose acetate succinate, carboxymethylethylcellulose, or cellulose acetophthalate, etc. may be used, preferably a methacrylate copolymer or hydroxypropylmethylcellulose phthalate may be mentioned.

In accordance with the present invention, to form a coating layer on the core material, that is, theophylline core granules, using the above coating agent, it is possible to use a known ordinary coating method etc., for example, it is possible to spray coat using a fluid bed coating method etc.

The coating agent for coating the theophylline core granules may be coated in one or more layers. In general, it is preferable to coat two layers. Note that, in coating, for example, it is possible to further coat the granules coated with a water-base coating agent with an alcohol-base coating agent or coat by an alcohol-base coating agent and then again coat by an alcohol-base coating agent. It is preferable to coat by a water-base coating agent and then coat by an alcohol-base coating agent. The coated granules obtained in this way have a coating of a preferably 5 to 50 parts by weight, more preferably 10 to 30 parts by weight, based upon 100 parts by weight of theophylline core granules.

The coated granules obtained by coating with a coating agent in this way are compressed for use as tablets by a general method together with a disintegrating excipient in an amount of preferably 1 to 25 parts by weight, more preferably 5 to 15 parts by weight, based upon 100 parts by weight of the theophylline in the coated granules. Further, the coated granules used for the tableting may be composed of mixtures of two or more types of different coated granules such as those with different amounts of coating and those with different compositions of coatings or number of layers. As the disintegrating excipient capable of using in the present invention, for example, corn starch, low substituted hydroxypropylcellulose, croscar mellose sodium, sodium carboxymethyl starch, etc. The disintegrating excipient hay be used in the powder state or formed into granules of a particle size of 50 to 1700 µm by for example a dry-granulation method etc.

The theophylline sustained release tablet according to the present invention is characterized in that, when subjected to in-vitro dissolution testing, it disintegrates into the original coated granules and disperses immediately after the start of the test. The theophylline is gradually dissolved from the disintegrated and dispersed coated granules to exhibit a sustained release action. Further, in the theophylline sustained release tablet of the present invention, the theophylline is mainly dissolved from the fractures and other broken parts formed in the coating when the coated granules are compressed. This dissolution is not affected much at all by the strength of the stirring in the dissolution testing and is not affected much at all by the compression pressure. Further, the dissolution of the theophylline from the theophylline sustained release tablet according to the present invention can be adjusted to a suitable rate by changing the composition of the coating agent, the amount of coating of the coating agent, and the ratio of mixture of coated granules with different coating amounts.

The theophylline sustained release tablet according to the present invention is obtained by coating core granules composed mainly of theophylline with a small amount of a coating agent and tableting the obtained coated granules with a small amount of a disintegrating excipient (for example, 1 to 25 parts by weight based upon 100 parts by weight of theophylline). Other additives are not necessarily required, so there is the advantage that the obtained tablets are smaller in size compared with conventional theophylline formulations.

Further, the theophylline sustained release tablet according to the present invention is easy to suitably control in the speed of dissolution of the theophylline, so when actually administered to humans, it is easy to design a theophylline sustained released tablet which can suppress an excessive rise in the blood level of the theophylline right after administration, make the optimal blood level be reached quickly, and maintain a stable effective blood level of the theophylline over a long time and possible to make the number of doses one to two times per day.

EXAMPLES

The present invention will now be explained in further detail below using Examples, but the scope of the present invention is not of course limited to these Examples.

Example 1

(1) 2000 g of theophylline powder, 20 g of sodium laurylsulfate, and 20 g of calcium stearate were mixed homogeneously and the mixture was granulated by a dry-granulation method to form the core granules. After granulation, the granules were milled to obtain about 1800 g of core granules having a size of 16 to 32 mesh.

(2) 200 g of a coating agent having the following composition using a commercially available aqueous coating agent of ethylcellulose (i.e., Aquacoat®, Asahi Kasei) and triethyl citrate was coated by a fluid-bed granulation coating machine on 400 g of the core granules obtained in (1) to prepare the coated granules.

| Composition | Weight (%) |
| --- | --- |
| Ethylcellulose | 17.4 |
| Cetanol | 1.8 |
| Sodium laurylsulfate | 0.8 |
| Triethyl citrate | 6.0 |
| Distilled water | 74.0 |
| (Total) | 100.0 |

(3) In the same way as (2), 400 g of the coating agent was sprayed onto 400 g of the core granules obtained in (1) to prepare coated granules.

(4) In the same way as (2), 700 g of a coating agent was sprayed onto 400 g of the core granules obtained in (1) to prepare the coated granules.

(5) 450 g of a coating agent having the following composition was further coated, by a fluid bed granulation coating machine, on 300 g of the coated granules obtained in (2) to prepare coated granules coated with two layers.

| Composition | Weight (%) |
| --- | --- |
| Ethylcellulose | 10.0 |
| Cetanol | 2.0 |
| Distilled water | 8.0 |
| Ethanol | 80.0 |
| (Total) | 100.0 |

(6) In the same way as (5), 450 g of a coating agent was sprayed onto 300 g of the coated granules obtained in (3) to prepare coated granules coated with two layers.

(7) In the same way as (5), 450 g of a coating agent was sprayed onto 300 g of the coated granules obtained in (4) to prepare coated granules coated with two layers.

(8) 500 g of low substituted hydroxypropylcellulose and 5 g of calcium stearate were homogeneously mixed and granulated by a dry-granulation method to prepare granules. After granulation, the granules were milled to obtain 200 g of granules having a size of 16 to 32 mesh.

(9) 284 g of the coated granules obtained in (5) and 30 g of the granules obtained in (8) were homogeneously mixed, then the mixture was compressed at 1.5 t using an irregular shaped punch to obtain tablets having a weight of 523 mg, a long diameter of 13 mm, a short diameter of 6.5 mm, and a thickness of 5.95 mm (i.e., tablet A-1.5).

(10) 300 g of the coated granules obtained in (6) and 30 g of the granules obtained in (8) were homogeneously mixed, then the mixture was compressed at 1.5 t using an irregular shape punch to obtain tablets having a weight of 550 mg, a long diameter of 13 mm, a short diameter of 6.5 mm, and a thickness of 6.25 mm (i.e., tablet B-1.5).

(11) 335 g of the coated granules obtained in (7) and 30 g of the granules obtained in (8) were homogeneously mixed, then the mixture was compressed at 1.5 t using an irregular shape punch to obtain tablets having a weight of 608 mg, a long diameter of 13 mm, a short diameter of 6.5 mm, and a thickness of 7.02 mm (i.e., tablet C-1.5).

Example 2

The coated granules obtained in (7) of Example 1 and the granules obtained in (8) of Example 1 were used in the same way as in (11) of Example 1 and compressed changing the compression pressure to 1.0 t and 2.0 t to obtain tablets (i.e., tablet C-1.0 and tablet C-2.0).

Example 3

107 g of the coated granules obtained in (4) of Example 1 and 10 g of the granules obtained in (8) in Example 1 were homogeneously mixed, then the mixture compressed at 1.5 t using an irregular shape punch to obtain tablets having a weight of 584 mg, a long diameter of 13 mm, a short diameter of 6.5 mm, and a thickness of 6.73 mm (i.e., tablet D-1.5).

Example 4

The coated granules obtained in (4) of Example 1 and the granules obtained in (8) of Example 1 were used in the same way as in Example 3 and tableted changing the compression pressure to 1.0 t and 2.0 t to obtain tablets (i.e., tablet D-1.0 and tablet D-2.0).

Example 5

(1) In the same way as in (2) of Example 1, 100 g of a coating agent was sprayed onto 300 g of the core granules obtained in (1) of Example 1 to prepare coated granules.

(2) In the same way as in (5) of Example 1, 390 g of a coating agent was sprayed onto 300 g of the coated granules obtained in (1) to prepare coated granules coated with two layers.

(3) 182 g of the coated granules obtained in (2) and 20 g of the granules obtained in (8) of Example 1 were homogeneously mixed, then the mixture was compressed at 1.5 t using an irregular shape punch to obtain tablets having a weight of 506 mg, a long diameter of 13 mm, a short diameter of 6.5 mm, and a thickness of 5.57 mm (i.e., tablet E-1.5).

Example 6

(1) In the same way as in (2) of Example 1, 360 g of a coating agent was sprayed onto 300 g of the core granules obtained in (1) of Example 1 to prepare coated granules.

(2) In the same way as in (5) of Example 1, 390 g of a coating agent was sprayed onto 300 g of the coated granules obtained in (1) to prepare coated granules coated with two layers.

(3) 210 g of the coated granules obtained in (2) and 20 g of the granules obtained in (8) of Example 1 were homogeneously mixed, then the mixture was compressed at 1.5 t using an irregular shape punch to obtain tablets having a weight of 575 mg, a long diameter of 13 mm, a short diameter of 6.5 mm, and a thickness of 6.53 mm (i.e., tablet F-1.5).

Example 7

91.1 g of the coated granules obtained in (2) of Example 5, 105 g of the coated granules obtained in (2) of Example 6, and 20 g of the granules obtained in (8) of Example 1 were homogeneously mixed, then the mixture was compressed at 1.5 t using an irregular shape punch to obtain tablets having a weight of 541 mg, a long diameter of 13 mm, a short diameter of 6.5 mm, and a thickness of 6.01 mm (i.e., tablet G-1.5).

Example 8

(1) 1500 g of theophylline powder and 15 g of calcium stearate were homogeneously mixed and the mixture granulated by a dry granulation method to prepare core granules. After granulation, about 1300 g of core granules having a size of 6 to 32 mesh was obtained.

(2) 300 g of a coating agent having the following composition using Aquacoat®, Eudragit L30D-550, and triethyl citrate was coated on 500 g of the core granules obtained in (1) by a fluid-bed granulation coating machine to prepare coated granules.

| Composition | Weight (%) |
| --- | --- |
| Ethylcellulose | 11.6 |
| Cetanol | 1.2 |
| Sodium laurylsulfate | 0.5 |
| Methacrylate copolymer | 2.7 |
| Triethyl citrate | 4.8 |
| Distilled water | 79.2 |
| (Total) | 100.0 |

(3) 300 g of a coating agent having the following composition using Aquacoat®, Eudragit L30D-55®, and triethyl citrate was coated on 500 g of the core granules obtained in (1) by a fluid bed granulation coating

| Composition | Weight (%) |
| --- | --- |
| Ethylcellulose | 12.2 |
| Cetanol | 1.3 |
| Sodium laurylsultate | 0.6 |
| Methacrylate copolymer | 2.0 |
| Triethyl citrate | 4.8 |
| Distilled water | 79.1 |
| (Total) | 100.0 |

(4) 300 g of coating agent having the following composition using ethylcellulose, hydroxypropylmethylcellulose phthalate (HP-50), and cetanol was further coated on 400 g of the coated granules obtained in (2) by a fluid-bed granulation coating machine to prepare coated granules coated with two layers.

| Composition | Weight (%) |
| --- | --- |
| Ethylcellulose | 5.3 |
| Hydroxypropylmethylcellulose phthalate | 2.7 |
| Cetanol | 0.8 |
| Distilled water | 11.2 |
| Ethanol | 80.0 |
| (Total) | 100.0 |

(5) In the same way as in (4), 300 g of a coating agent was sprayed onto 400 g of the coated granules obtained in (3) to prepare coated granules coated with two layers.

(6) 300 g of low substituted hydroxypropylcellulose and 3 g of calcium stearate were used in the same way as in (8) of Example 1 to obtain 100 g of granules having a size of 16 to 32 mesh.

(7) 91.6 g of the coated granules obtained in (4) and 10 g of the granules obtained in (6) were homogeneously mixed, then the mixture was compressed using a circular punch to obtain tablets having a weight of 254.0 mg, a diameter of 8 mm, and a thickness of 5.29 mm (i.e., tablet H).

(8) 89.3 g of the coated granules obtained in (5) and 10 g of the granules obtained in (6) were homogeneously mixed, then the mixture was compressed using a circular punch to obtain tablets having a weight of 248.3 mg, a diameter of 8 mm, and a thickness of 5.24 mm (i.e., tablet I).

Test Example 1

A dissolution test was performed according to the second method (i.e., paddle method) of the 13th revised Japanese Pharmacopoeia (hereinafter referred to as the "Japanese Pharmacopoeia") dissolution testing method using the tablets prepared by the Examples as samples and using a Japanese Pharmacopoeia disintegration test method No. 2 solution (hereinafter referred to as "Japanese Pharmacopoeia 2 solution"). The effluent of the samples was sampled with the elapse of time after the start of the test. The sampled solutions were measured for absorbance at 271 nm after dilution with 0.1N hydrochloric acid and the dissolution rates were determined. The results are shown in FIG. 1 to FIG. 4.

From the results shown in FIG. 1, it is clear that the formulation of the present invention has a lower dissolution rate, as the amount of the coating agent is increased. From the results shown in FIG. 2 and FIG. 3, it is recognized that, when comparing the dissolution rates of formulations coated with two layers (i.e., tablets C-1.0 to C-2.0) and formulations coated with a single layer (i.e., tablets D-1.0 to D-2.0), the former have lower dissolution rates and further are not so susceptible to the effects of the speed of the paddle, that is, the stirring strength, and the effects of the compression pressure.

Figure 4:
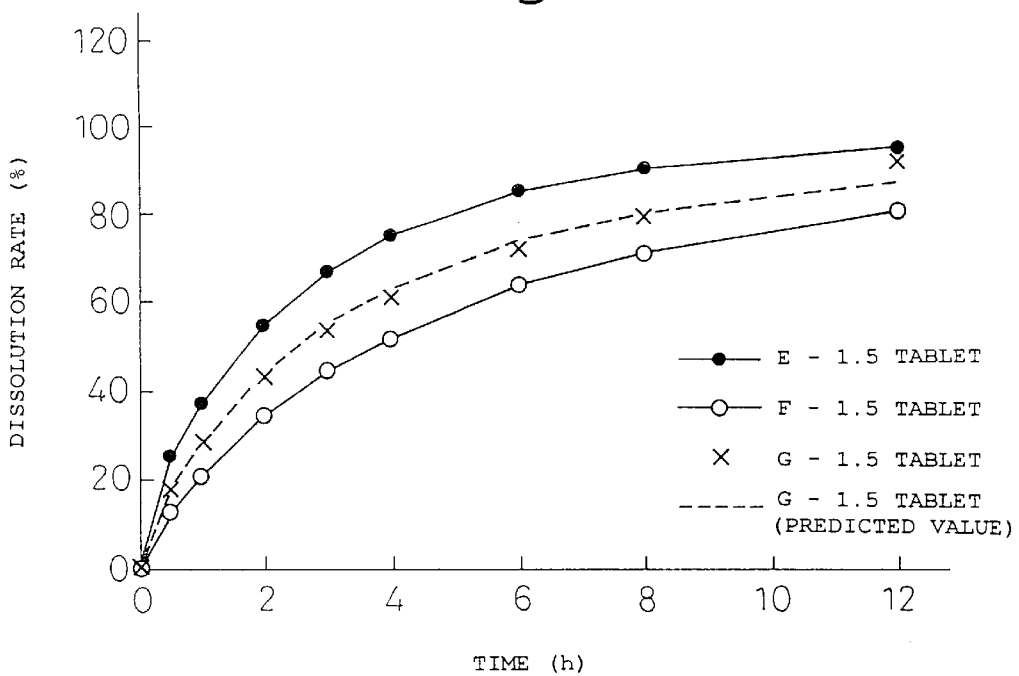
FIG. 4 is a graph showing the results of dissolution testing of a tablet E-1.5, a tablet F-1.5, and a tablet G-1.5 obtained in Examples 5 to 7 (i.e., second method, 50 revolutions, Japanese Pharmacopoeia 2 solution) and a graph of the dissolution behavior of the tablet G-1.5 predicted from the results of the dissolution testing of the tablet E-1.5 and tablet F-1.5.

Further, from the results of FIG. 4, the dissolution rate of the tablet (i.e., tablet G-1.5) prepared by mixing two types of coated granules with different coating amounts substantially matches the curve predicted from the dissolution rates of the tablets prepared from only single types of coated granules (i.e., tablets E-1.5 and F-1.5). Accordingly, it was recognized that, by mixing coated granule having different coating amounts to prepare the tablets, it is possible to adjust the dissolution rate as desired.

Test Example 2

A dissolution test was performed according to the second method of the Japanese Pharmacopoeia dissolution test method in the same way as in Test Example 1 using the tablets prepared by the Examples (i.e., tablet H and tablet I) as samples and using a Japanese Pharmacopoeia disintegration test method No. 1 solution (hereinafter referred to as "Japanese Pharmacopoeia 1 solution") and Japanese Pharmacopoeia 2 solution. The dissolution rate was determined in the same way as in Test Example 1. The results are shown in FIG. 5.

From the results shown in FIG. 5, the tablet H had a faster dissolution rate of the theophylline with the Japanese Pharmacopoeia 2 solution rather than the Japanese Pharmacopoeia 1 solution. However, the Tablet I exhibited almost the same dissolution behavior with the Japanese Pharmacopoeia 1 solution and Japanese Pharmacopoeia 2 solution. That is, since it is possible to freely change the dissolution behavior of the theophylline by changing the ratio of composition of the Aquacoat® and Eudragit L30D-55®, it can be expected to achieve a similar dissolution rate in the stomach and intestines by changing the ratio of composition to the coating materials or to increase the dissolution rate to the theophylline in the intestines over the stomach so as to make all of the theophylline dissolve in the digestive tract, whereby the bioavailability is increased.

INDUSTRIAL APPLICABILITY

The sustained release tablet of theophylline according to the present invention has a stable dissolution rate of theophylline which is resistant to the effect of the compression pressure at the time of production or the strength of stirring at the time of dissolution testing. Further, the rate of dissolution of the theophylline can be suitably adjusted to the desired dissolution rate by the ratio of mixing of two or more types of coated granules having different compositions of the coating or amounts of coating. Further, it is possible to easily design a formulation of a type for administration once or twice a day. Further, compared with a multiple unit type tablet of the past, it is possible to prepare the tablet by a relatively simple formulation and possible to make a small sized tablet since no additives other than the disintegrating excipient are necessarily required.

What is claimed is:

1. A theophylline sustained release tablet comprising (i) core granules having a theophylline content of 98% or more, (ii) at least one coating film layer composed of a hydrophobic material, and a plastic excipient to form coated granules and (iii) a disintegrating excipient, and coated granules and said disintegrating excipient being compression molded to form the theophylline sustained release tablet, wherein the sustained release action is obtained by the tablet disintegrating into the coated granules that are dispersed immediately and the theophylline is gradually dissolved from the dispersed coated granules.

2. A theophylline sustained release tablet as claimed in claim 1, wherein the coated granules are obtained by coating core granules mainly composed of theophylline coated with at least one layer coating film composed of a hydrophobic material, an enteric polymer material and a plastic excipient.

3. A theophylline sustained release tablet as claimed in claim 1 or 2, wherein the core granules mainly composed of theophylline have a high hardness, a particle size of 50 to 1700 μm.

4. A theophylline sustained release tablet as claimed in claim 1 or 2, wherein the coated granules are coated with two layers.

5. A theophylline sustained release tablet as claimed in claim 1 or 2, wherein the coated granules are a mixture of at least two coated granules having different coating compositions or coating amounts.

6. A theophylline sustained release tablet as claimed in claim 1 or 2, wherein the hydrophobic material in the coating is a water insoluble polymer material.

7. A theophylline sustained release tablet as claimed in claim 1 or 2, wherein the plastic excipient in the coating is triethyl citrate, glyceryl fatty acid ester, cetanol, hardened castor oil, hardened rapeseed oil, or carnauba wax.

8. A theophylline sustained release tablet as claimed in claim 2, wherein the enteric polymer material in the coating is a methacrylic acid copolymer or hydroxypropylmethylcellulose phthalate.

9. A theophylline sustained release tablet as claimed in claim 1 or 2, wherein the amount of the coating in the coated granules is 5 to 50 parts by weight based upon 100 parts by weight of the core granules.

10. A theophylline sustained release tablet as claimed in claim 1 or 2, wherein the amount of the disintegrating excipient is 5 to 15 parts by weight based upon 100 parts by weight of the theophylline.

11. A theophylline sustained release tablet comprising (i) core granules having a theophylline content of 98% or more, (ii) 5 to 50 parts by weight, based upon 100 parts by weight of the core granules, of at least one coating film layer composed of a hydrophobic material and a plastic excipient to form coated granules, and (iii) 1 to 25 parts by weight, based upon parts by weight of theophylline of a disintegrating excipient, and coated granules and said disintegrating excipient being compression molded to form the theophylline sustained release tablet, wherein the the sustained release action is obtained by the tablet disintegrating into the coated granules that are dispersed immediately and the theophylline is gradually dissolved from the dispersed coated granules.

12. A theophylline sustained release tablet as claimed in claim 6, wherein the water insoluble polymer material is selected from the group consisting of ethylcellulose, ethyl acrylate-methyl methacrylate copolymers, and amino alkyl-methacrylate polymers.

13. A theophylline sustained release tablet as claimed in claim 11, wherein the coated granules are obtained by coating core granules mainly composed of theophylline coated with at least one layer coating film composed of a hydrophobic material, an enteric polymer material, and a plastic excipient.

* * * * *